United States Patent
Messina et al.

(10) Patent No.: US 7,463,765 B2
(45) Date of Patent: Dec. 9, 2008

(54) SYSTEM AND METHOD FOR DETECTING AND REPORTING FABRICATION DEFECTS USING A MULTI-VARIANT IMAGE ANALYSIS

(75) Inventors: Vincent J. Messina, Pelham, NH (US); Donald J. Ronning, Pelham, NH (US)

(73) Assignee: Lamda-Lite Enterprises Incorporated, Pelham, NH (US)

( * ) Notice: Subject to any disclaimer, the term of this patent is extended or adjusted under 35 U.S.C. 154(b) by 960 days.

(21) Appl. No.: 10/785,213

(22) Filed: Feb. 24, 2004

(65) Prior Publication Data

US 2004/0165762 A1    Aug. 26, 2004

Related U.S. Application Data

(60) Provisional application No. 60/450,053, filed on Feb. 25, 2003.

(51) Int. Cl.
    G06K 9/00    (2006.01)
(52) U.S. Cl. .................. 382/149; 382/144; 382/218
(58) Field of Classification Search ............ 250/559.22; 348/218.1; 382/141, 144, 145, 147, 149, 382/151, 218, 219, 276
    See application file for complete search history.

(56) References Cited

U.S. PATENT DOCUMENTS

| | | | | |
|---|---|---|---|---|
| 4,532,650 | A | 7/1985 | Wihl et al. ................ 382/8 |
| 4,805,123 | A | 2/1989 | Specht et al. ............. 364/559 |
| 5,125,040 | A | 6/1992 | Matsui et al. ............. 382/34 |
| 5,129,009 | A | 7/1992 | Lebeau .................... 382/8 |
| 5,452,369 | A | 9/1995 | Lionti et al. .............. 382/141 |
| 5,537,669 | A * | 7/1996 | Evans et al. .............. 382/141 |
| 5,574,800 | A | 11/1996 | Inoue et al. ............... 382/149 |
| 5,619,588 | A | 4/1997 | Yolles et al. .............. 382/149 |
| 5,848,189 | A | 12/1998 | Pearson et al. ............ 382/218 |
| 5,850,466 | A * | 12/1998 | Schott .................... 382/141 |
| 5,859,698 | A | 1/1999 | Chau et al. ............... 356/237 |
| 5,887,077 | A | 3/1999 | Bongardt et al. .......... 382/149 |
| 6,069,971 | A | 5/2000 | Kanno et al. ............. 382/144 |
| 6,272,236 | B1 * | 8/2001 | Pierrat et al. ............. 382/144 |
| 6,295,374 | B1 | 9/2001 | Robinson et al. .......... 382/218 |
| 6,396,945 | B1 * | 5/2002 | Ishii ..................... 382/149 |
| 6,444,382 | B1 | 9/2002 | Sarig et al. .............. 430/30 |
| 6,477,275 | B1 | 11/2002 | Melikian et al. .......... 382/217 |
| 6,480,627 | B1 | 11/2002 | Mathias et al. ........... 382/224 |
| 6,539,106 | B1 * | 3/2003 | Gallarda et al. .......... 382/149 |
| 6,622,135 | B1 * | 9/2003 | De Tremiolles et al. .... 706/20 |
| 6,693,664 | B2 * | 2/2004 | Neumann ................ 348/126 |

(Continued)

*Primary Examiner*—Gregory M Desire
(74) *Attorney, Agent, or Firm*—Downs Rachlin Martin PLLC (57) ABSTRACT

An inspection process and an inspection system (600) that utilize a plurality of residual defect signals 252(1), 252(2), . . . 252(n) to identify and report defects of interest in a copy (116) of a standard (112). The process includes performing a multi-variant defect extraction method (200) that includes applying a number n of pre-determined transforms to both a data file (232) containing the standard and an image file (204) containing the copy of the standard so as to create a plurality of conditioned data files (244(1), 244(2), . . . 244(n)) and a plurality of conditioned image files (216(1), 216(2), . . . 216(n)). The plurality of residual defect signals are extracted from these conditioned files. A defect analysis and reporting method (500) utilizes the residual defect signals to report defects contained in two or more of the residual defect signals.

36 Claims, 8 Drawing Sheets

U.S. PATENT DOCUMENTS

| | | | |
|---|---|---|---|
| 6,778,695 B1 * | 8/2004 | Schellenberg et al. | 382/144 |
| 6,865,288 B1 * | 3/2005 | Shishido et al. | 382/145 |
| 6,882,745 B2 * | 4/2005 | Brankner et al. | 382/144 |
| 6,973,208 B2 * | 12/2005 | Kuwabara | 382/145 |
| 7,065,239 B2 * | 6/2006 | Maayah et al. | 382/145 |
| 7,218,771 B2 * | 5/2007 | Gilat-Bernshtein et al. | 382/147 |
| 2002/0126888 A1 * | 9/2002 | Vacca et al. | 382/145 |
| 2002/0191833 A1 | 12/2002 | Kim | 382/149 |
| 2003/0016858 A1 | 1/2003 | DeYong et al. | 382/149 |
| 2003/0048957 A1 | 3/2003 | Dai et al. | 382/260 |
| 2004/0106868 A1 * | 6/2004 | Liew et al. | 600/442 |
| 2004/0120569 A1 * | 6/2004 | Hung et al. | 382/144 |
| 2004/0165762 A1 * | 8/2004 | Messina et al. | 382/141 |
| 2004/0247171 A1 * | 12/2004 | Hashimoto et al. | 382/141 |
| 2008/0107328 A1 * | 5/2008 | Chen et al. | 382/149 |

* cited by examiner

SYSTEM AND METHOD FOR DETECTING AND REPORTING FABRICATION DEFECTS USING A MULTI-VARIANT IMAGE ANALYSIS

RELATED APPLICATION DATA

This application claims the benefit of priority of U.S. Provisional Patent Application Ser. No. 60/450,053, filed Feb. 25, 2003, and titled "Multi-Variant Analysis for Enhanced Defect Detection and Reporting," that is incorporated by reference herein in its entirety.

FIELD OF THE INVENTION

The present invention generally relates to the field of image analysis. In particular, the present invention is directed to a system and method for detecting and reporting fabrication defects using a multi-variant image analysis.

BACKGROUND OF THE INVENTION

Accurate and reliable defect inspection is vital to the successful fabrication processes. Fabrication processes strive to faithfully reproduce an intended design, or standard, that is typically represented by the computer aided design (CAD) pattern created by a designer. It is generally known that deformation of the standard occurs in fabricating various works (i.e., making copies of the standard), such as artworks, reticles, photomasks and production parts of electronic, semiconductor, display, micro-electromechanical system, hard disk and nanotechnology workpieces, devices, and continuous web processes, among others. Fabrication processes are often highly sensitive to: 1) material defects; 2) contamination by particles introduced by various processing tools; 3) various deleterious effects associated with unwanted environmental contaminants; 4) residual films; 5) extra or missing materials; and 6) other defects resulting from fabrication process variations.

Typically, each layer (i.e., copy) in a production part has been formed to closely represent the specific structures intended according to that part's particular design, as represented by the standard. Often, a production part is produced through its own corresponding mask, reticle, photomask or artwork to properly form regions of light that are subsequently directed onto a substrate. Depending on the type of resist (e.g., positive or negative) that is coated upon the substrate, the regions of light formed by the mask correspond to either the specific structures formed on the substrate or the spaces between these structures. The corresponding mask, reticle, photomask or artwork is patterned in either a 1:1 representation of the standard, or a derivative of the standard that corresponds to the structures formed on the substrate. Other times, the production part is produced through the direct ablation, machining, milling, etching or deposition of material so that the result is representative of the designed data structure.

Conventional inspection systems are designed to identify defects by comparing an image of the artwork, reticle, photomask or production part, i.e., a copy, with a standard that is either the designed data structure (the designer's original intention), or a "golden" image of a part being inspected. Any dissimilarity is reported as a defect.

It has been known that spurious "false" defects are reported by all automatic optical inspection systems. The sources of the false defects are many, including those related to the production process of the piece to be inspected, the defect observation system, the defect image analysis methodology, the defect classification methodology and others. One approach to this problem, disclosed in U.S. Pat. No. 4,805,123 to Specht, et al., is to resample and detect the differences between the samples to reduce the effect of false reports. A different approach to this problem, disclosed in the U.S. Pat. No. 4,532,650 to Wihl, et al., uses an algorithm specific to defect types (defects at pattern corners). Yet another approach to this problem disclosed in U.S. Pat. No. 6,480,627 to Mathias et al., is to use an evolutionary (learning) algorithm implemented in a neural net that effects image characterization and classification.

Typical conventional inspection systems employ simple image, single-level analysis. The quality of the inspection can be considered to be limited to the signal-to-noise ratio achievable by the system. Inspection of artworks, reticles, photomasks and parts production of electronic, semiconductor, display, micro-electromechanical system, hard disk, and nanotechnology processes using the above described single stage process has a limited capability to reliably identify small sized defects of interest. While any single inspection technique may be very capable of detecting a certain type defect, it is less likely to be capable of detecting other types of defects. For any single inspection technique, a portion of the defects may be readily detectable, while another portion of the defects is either poorly detected or undetectable by the inspection system. A differing inspection technique may have different sensitivity to the same group of defects. Furthermore, any single inspection technique may accurately identify the presence of differing types of defects but be incapable of differentiating between the differing types of defects. Thus, what is needed is an improved method of defect detection and reporting technique for detecting and differentiating defects of interest that are difficult to accurately detect using current inspection techniques while minimizing the reporting of non-defective areas being reported as defective. The present invention satisfies that need, as well as others, and overcomes deficiencies in current inspection techniques.

SUMMARY OF THE INVENTION

In one aspect, the present invention is directed to a method of inspecting a copy for defects of interest. The method comprises the steps of providing an image signal containing a region of interest of the copy and transforming the image signal by a plurality of transform functions so as to obtain a plurality of conditioned image signals. A plurality of residual defect signals are extracted using the plurality of conditioned image signals to determine the presence of defects of interest. Each residual defect signal of the plurality of residual defect signals corresponds to a respective one of the plurality of conditioned image signals. A rule-based analysis is performed on the plurality of residual defect signals.

In another aspect, the present invention is directed to a defect detection and classification system for inspecting items for defects of a plurality of defect types. The system comprises a defect detection device operatively configured to perform a plurality of analyses of a region of interest and provide at least one signal representing each type of defect. Each of the plurality of analyses operates to enhance at least one of the plurality of defect types. A rule-based logic system is in communication with the defect detection device and is operatively configured to receive and process the plurality of signals and for classifying defects within the region of interest. Each of the plurality of signals is compared to the others of the plurality of signals and is associated to one or more of the plurality of signals having characteristics similar to that one of the plurality of signals.

BRIEF DESCRIPTION OF THE DRAWINGS

For the purpose of illustrating the invention, the drawings show a form of the invention that is presently preferred. However, it should be understood that the present invention is not limited to the precise arrangements and instrumentalities shown in the drawings, wherein.

DETAILED DESCRIPTION OF THE DRAWINGS

Figure 1:
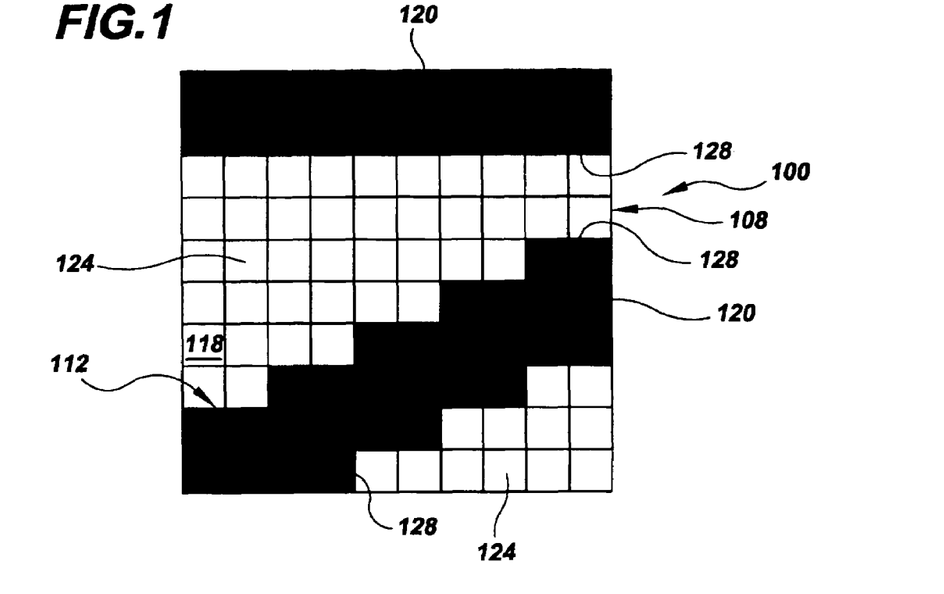
FIG. 1 is an image of a region of interest of a standard.
Figure 2:
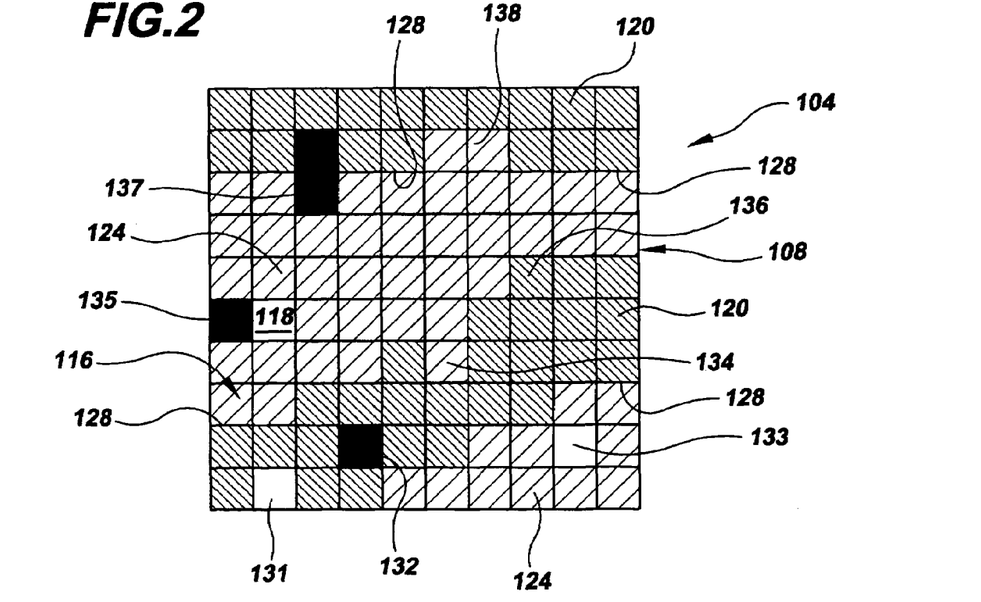
FIG. 2 is an image of the region of interest of a copy corresponding to the standard of FIG. 1.

Referring now to the drawings, FIGS. 1 and 2 show images 100, 104 of a region of interest 108 of, respectively, a standard 112 and a copy 116 of the standard. As discussed above in the Background section, standard 112 may be a data file, or signal, e.g., a CAD file, used to create copy 116 directly or to create an intermediate structure (not shown), such as a photomask, reticle, engraving or pattern, among other intermediate structures, that is subsequently utilized in making the copy. In other forms, standard 112 may be a "golden image" of a production part (not shown), intermediate structure or other item corresponding to copy 116. In yet other forms, standard 1 12 can be any data file or signal containing information against which a reproduction or recreation of the standard, i.e., copy 116, may be compared. In this connection, it is noted that the term "copy" as used herein is not limited to a strict original/copy relationship. The only relationship intended herein and in the claims appended hereto between the terms "standard" and "copy" is that a copy is the subject of a comparison to a standard to determine differences, if any, that exist between the copy and the standard. These differences are often, but not necessarily, denoted as defects. As such, the term "defects" is used herein and in the appended claims for convenience. However, the term "defects" must not be construed as limiting the present invention to defect detection, but rather difference detection in general.

As discussed below in detail, the present invention is directed to an inspection system (FIG. 10) and a process for detecting and reporting defects in image 104 of copy 116 relative to image 100 of standard 112, and, ostensibly, defects in the copy itself. The process generally includes two broad steps, a first step of extracting information regarding defects in image 104 of copy 116 (see method 200 of FIG. 3 and accompanying description) and a second step analyzing and reporting these defects (see method 500 of FIG. 9 and accompanying description). In one embodiment, the first step is accomplished by conditioning each of images 100, 104 using a plurality of a number n of predetermined transfer functions, or transforms, to condition the various features within region of interest 108 to enhance corresponding types of defects. Transforms commonly utilized to condition images include, but not limited to morphology, geometric, convolution, thresholding operations. Those skilled in the art will recognize that a number of varying transforms maybe applied in different sequences to determine the defects of interest to the end user. The process of performing these multiple conditionings may be referred to as "multi-variant conditioning."

By using such a series of predetermined transfer functions to condition region of interest 108 of images 100, 104 of both copy 116 and corresponding standard 112, a defect signal having a signal-to-noise (S/N) ratio higher than the S/N ratios achievable with conventional single-level image analyses can be obtained. The predetermined transform functions become parameters that increase the number of degrees of freedom of the inspection at region of interest 108, resulting in a reduction in the uncertainty of the reported results at the region of interest. The result of each predetermined transform analysis becomes a sub-component of the second step, which generally involves a larger multi-variant analysis for analyzing and reporting the observed defects.

Figure 10:
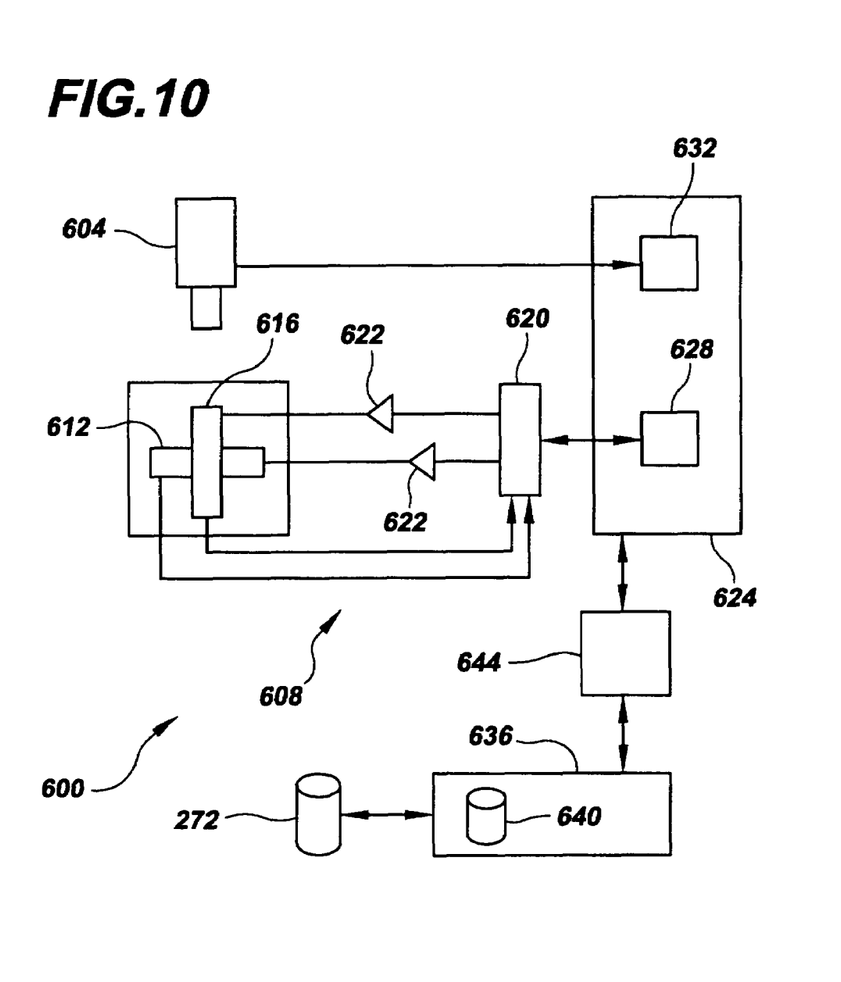
FIG. 10 is a high-level schematic diagram of an inspection system of the present invention.

The resulting quality of the multi-variant inspection of the present invention can be considered to be superior to any single-level analysis due to the resulting increase in the composite S/N ratio of the multi-variant conditioning. The reliability of determination of the presence of one or more defects of interest can be increased through the identification of the sub-components of the multi-variant analysis. The enhanced S/N ratio of the composite analysis reduces the probability of incorrectly reporting a defect. Regarding a system of the present invention, one embodiment of a system (600) for performing the process of the present invention is shown in FIG. 10 and discussed in accompanying text.

Returning to FIGS. 1 and 2, each image 100, 104 is shown as being a 10×10 unit array, e.g., an array of 10 pixels (118) by 10 pixels. Referring particularly to FIG. 1, standard 112 may be a CAD file that generally includes a defined structure 120, an absence 124 of the defined structure and edges 128 between the defined structure and the absence of the defined structure. As discussed above, standard 112 may be used to create any number of items, e.g., a photomask for a lithography process used in making the wiring layers of microprocessor die. In this case, the photomask would be copy 116 of FIG. 2. If copy 116 is a photomask, defined structure 120 may be objects in the CAD file that represent opaque portions of the photomask used to pattern a photoresist with the locations of the wires. Correspondingly, absence 124 of defined structure 120 may be the transparent portions of the photomask used to pattern the photoresist with regions where wires will not be present. In this example, copy 116 may also be the processed photoresist layer or the finished metal layer made using the photomask.

It is noted that in FIG. 1 pixels 118 corresponding respectively to defined structure 120 and absence 124 of the defined structure are shown as being highly contrasted with one another for convenience, but, depending upon the type of standard 112 and/or image 100 of the standard, this high contrast may be inherent. For example, a CAD file may contain only objects, e.g., lines and shapes, such that at any given location within standard 112 the information corresponding to that location is binary, i.e., either an object is present there or it is not. Those skilled in the art will recognize that the contrast need not be so sharp, depending upon the subject matter of standard 112 or the character of image 100 of the standard.

FIG. 2, on the other hand, shows copy 116 of standard 112 at the same 10×10 unit region of interest 108 shown in FIG. 1. In the example discussed above relative to standard 112, copy 116 may be a photomask, processed resist layer or metal layer made using the standard and/or the photomask. Correspondingly, image 104 of copy 116 may be acquired using an image capturing device, such as detector 604 of inspection system 600 shown in FIG. 10. A number of differences between image 104 of copy 116 of FIG. 2 and image 100 of standard 112 of FIG. 1 can be seen. For example, defined structure 120 is generally lighter in FIG. 2 than in FIG. 1. Similarly, absence 124 of defined structure 120 is generally darker in FIG. 2 than in FIG. 1. These differences may be due to various performance aspects of inspection system 600 (FIG. 10) and/or characteristics, e.g., reflectance or absorbance, among others, of the corresponding features of the item, e.g., photomask, into which copy 116 is embodied. These differences may be corrected as discussed below in conjunction with FIG. 3.

Other notable differences include the presence of defects 131-138 in region of interest 108 of image 104 of FIG. 2. Defects 131-138 may be caused by inspection system 600 (FIG. 10) or may be caused during the fabrication of copy 116 for any of a number of reasons, such as: 1) material defects; 2) contamination by particles introduced by various processing tools; 3) various deleterious effects associated with unwanted environmental contaminants; 4) residual films; 5) extra or missing materials; and 6) other defects resulting from fabrication process variations. When standard 112 and copy 116 are characterized as having one or more defined structures 120, one or more absences 124 of the defined structure(s) or one or more edges 128 of the defined structure(s), any defects may generally be grouped into six types: 1) missing component of defined structure (e.g., defect 131); 2) extra component of the defined structure (e.g., defect 132); 3) missing component of absence of the defined structure (e.g., defect 133); 4) extra component of the absence of the defined structure (e.g., defect 135); 5) missing component in edge of the defined structure (e.g., defects 134, 138); and 6) extra component in the edge of the defined structure (e.g., defects 136, 137). It is noted that the characterization of standard 112 and copy 116 and corresponding defect types mentioned above are by no means exhaustive of the universe of characterizations and defect types that may be detected and reported using the present invention. They are merely used to simplify the explanation of the invention. Those skilled in the art will understand that the scope of the present invention extends to any type of image characterization and type of defect that can be measured by comparing an image of a copy to a standard (or an image of the standard).

Figure 3:
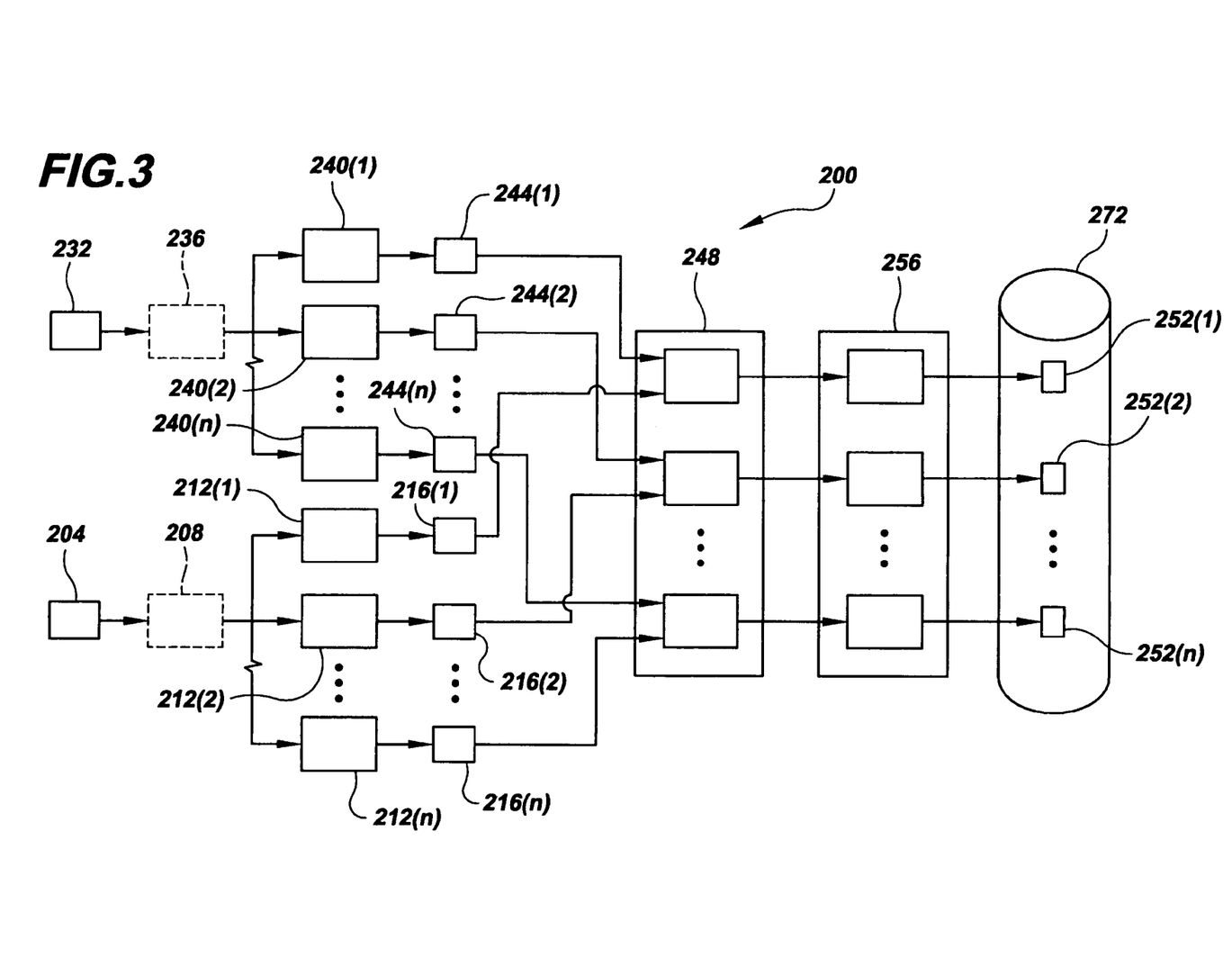
FIG. 3 is a flow chart illustrating a multi-variant defect data extraction method of the present invention for extracting data regarding defects in the region of interest of the copy of FIG. 2.

Referring now to FIG. 3, and also to FIGS. 1 and 2, FIG. 3 illustrates a multi-variant defect data extraction method 200 of the present invention that may be used to obtain the data to be used in the defect analysis and reporting method 500 discussed below in detail relative to FIG. 9. Generally, defect data extraction method 200 may proceed as follows. Once a region of interest, e.g., region of interest 108 of FIG. 2, of a copy, e.g., copy 116 of FIG. 2, has been captured in an image file 204, the image file may be pre-conditioned at step 208 as needed to correct the image file for further processing in accordance with the invention. In this connection, it is noted that image file 204 may contain only a single region of interest to be processed at this time. Alternatively, image file 204 may be a gross image file containing image 104 of entire copy 116 or a portion of the copy smaller than the copy but larger than the region of interest. In these cases, it may be desirable to extract only one region of interest at a time. Pre-conditioning step 208 may include, e.g., applying one or more geometric corrections to image file 204 to correct any distortions introduced by the optical, mechanical and/or other systems used to capture image 104 of copy 116, and/or applying one or more photometric corrections to the image file to correct for variants such as illumination, reflectance and electro-optic component variations, among others.

At steps 212(1), 212(2), . . . 212($n$), image file 204 may be further conditioned using a corresponding number n of predetermined transforms so as to create n conditioned image files 216(1), 216(2), . . . 216($n$). Each predetermined transform may be selected to enhance detection of a corresponding type of defect, or in some cases a group of defect types, so as to optimize detection of such defect type(s). As those skilled in the art will appreciate, the number of predetermined transforms and the transforms themselves may be selected according to any number of criteria. For example, if three types of defects are appropriate for a certain inspection and each of these types is efficiently detected by a corresponding transform, then image file 204 may be conditioned at steps 212(1), 212(2), 212($n$)(n=3) using three transforms to create three conditioned image files 216(1), 216(2), 216($n$)(n=3). In alternative inspections wherein certainty of the presence of a type of defect is enhanced by using multiple different transforms, image file 204 may be transformed by such multiple transforms. For example, if copy 116 contains two types of defects and it is beneficial to utilize three transforms relative to one of the types, but only one transform relative to the other type, image file 204 would be transformed by four transforms so as to create three conditioned image files. In yet other alternative inspections, two or more types of defects may be detected using only one transform. For example, in the case wherein four types of defects are the subject of inspection, two types may be detected with one transform and the other two types with one transform each, such that the total number of transforms and conditioned image files is four. Those skilled in the art will understand that these examples are by no means either exhaustive or limiting relative to the broad scope of the invention, and that it is not practical to list all possible alternatives due to the wide variety of defect types and transforms that are available for detecting such defect types.

Regarding exemplary standard 112 and copy 116 of FIGS. 1 and 2, respectively, it was noted above that the copy (or image 104) may contain three general types of defects: 1) defects occurring within defined structure 120; 2) defects occurring within absence 124 of the defined structure; and 3) defects occurring on edge 128 of the defined structure. If each of these three defect types is adequately detected by transforming image file 204 by a corresponding predetermined transform, then at step 212(1), 212(2), 212($n$) (n=3) the image file containing image 104 of copy 116 may be conditioned by each of the transforms so as to create three conditioned image files 216(1), 216(2), 216($n$) (n=3).

Figure 4A:
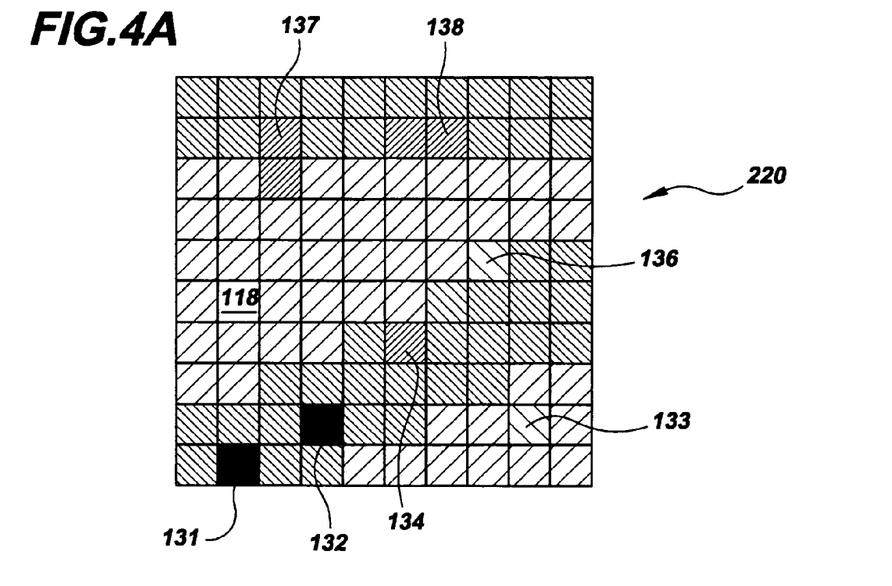
FIG. 4A is a conditioned image of the region of interest of FIG. 2 conditioned to enhance defects occurring within the defined structure present within the region of interest.
Figure 5A:
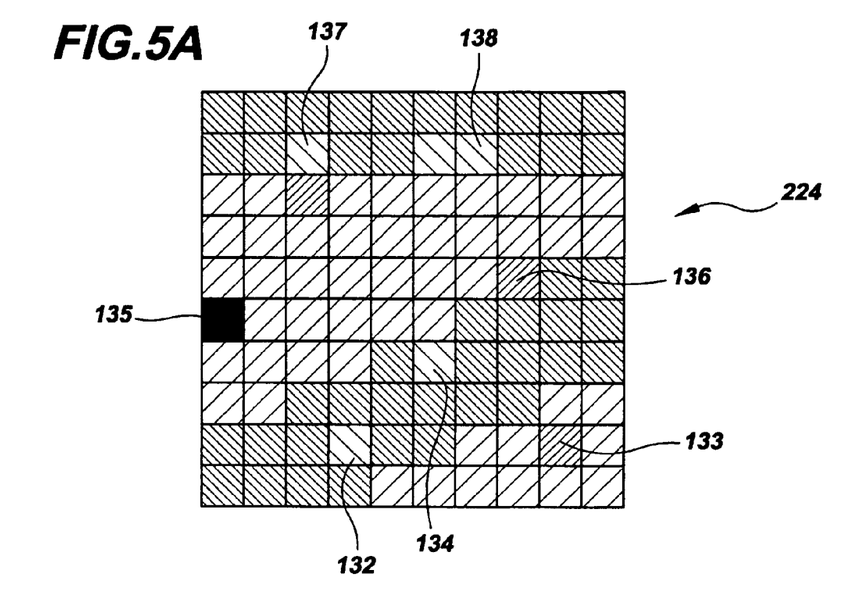
FIG. 5A is a conditioned image of the region of interest of FIG. 2 conditioned to enhance defects occurring in the absence of the defined structure present within the region of interest.

For example, referring to FIG. 4A, and also to FIG. 2, FIG. 4A illustrates a first conditioned image 220 conditioned by applying a first transform to image file 204 that enhances detection of defects occurring within defined structure 120. A suitable transform may be a threshold operation at a level equal to the pixel value of structure, thus to differentiate between structure (lighter pixels) from no-structure (darker structure). Of course, those skilled in the art will recognize that other transforms are suitable for enhancing detection of defects occurring within defined structure 120. Conditioned image 220 is contained in conditioned image file 216(1). It is noted that the level of enhancement of defects is represented in FIG. 5A by the relative darkness of each unit, i.e., pixel 118 in the example, containing a defect. Consequently, defects 131, 132 that are within defined structure 120 are relatively very dark. In this example, it is noted that the first transform is also capable of capturing at least some of the defects outside defined structure 120, particularly those defects that are at edge 128 of the defined structure. Accordingly, defects 133, 134, 136, 137, 138 are also discerned by the first transform, but at a lower level of enhancement than defects 131, 132 fully contained within defined structure 120. Defect 135 (FIG. 2), which is neither within defined structure 120 nor proximate edge 128 of the defined structure, is not discerned by the first transform. This example is illustrative and by no means limiting relative to the scope of the present invention.

Referring to FIG. 5A, and also to FIG. 2, FIG. 5A illustrates a second conditioned image 224 conditioned by applying a second transform to image file 204 that enhances detection of defects occurring in absence 124 of defined structure 120. A suitable transform may be an image inversion and threshold operations, the threshold operation at a level equal to the pixel value of no-structure, thus to differentiate no-structure from structure. Of course, those skilled in the art will recognize that other transforms are suitable for enhancing detection of defects occurring in absence 124 of defined structure 120. Conditioned image 224 is contained in conditioned image file 216(2). Again, the level of enhancement of defects is represented in FIG. 5A by the relative darkness of each unit, i.e., pixel 118, containing a defect. Consequently, defects that are within absence 124 of defined structure 120 are relatively dark, particularly defect 135 that is not immediately adjacent edge 128 of the defined structure. It is noted that the second transform is also capable of capturing at least some of the defects outside absence 124 of defined structure 120, particularly those defects that are at edge 128 of the defined structure. Accordingly, defects 132, 133, 134, 136, 137, 138 are also discerned by the second transform, but at a lower level of enhancement than defects fully contained within absence 124 of defined structure 120. Defect 131 (FIG. 2), which is neither within absence 124 of defined structure 120 nor proximate edge 128 of the defined structure, is not discerned by the second transform.

Figure 6A:
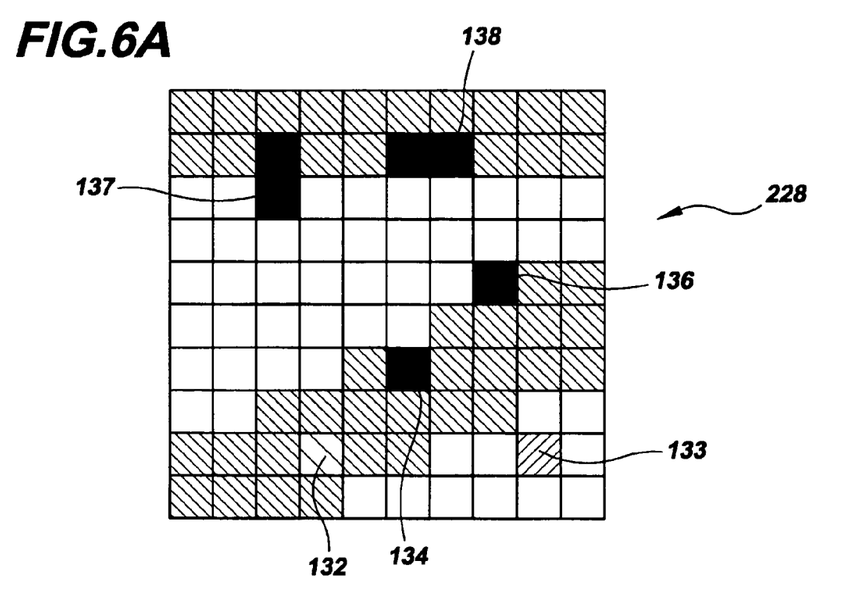
FIG. 6A is a conditioned image of the region of interest of FIG. 2 conditioned to enhance defects occurring on the edges of the defined structure present within the region of interest.

Referring now to FIG. 6A, and also to FIG. 2, FIG. 6A illustrates a third conditioned image 228 conditioned by applying a third transform to image file 204 that enhances detection of defects occurring on edge 128 of defined structure 120. A suitable transform may be threshold operation at a level equal to the pixel value of the structure on the edge of structure, thus to differentiate between structure and edge of structure. Of course, those skilled in the art will recognize that other transforms are suitable for enhancing detection of defects occurring on edge 128 defined structure 120. Conditioned image 228 is contained in conditioned image file 216 (n) (n=3). Again, the level of enhancement is represented in FIG. 6A by the relative darkness of each unit, i.e., pixel 118, containing a defect. Consequently, defects 134, 136, 137, 138 that are on edge 128 of defined structure 120 are relatively very dark. It is noted that the third transform is also capable of capturing at least some of the defects located away from edge 128 of defined structure 120, particularly those defects that are relatively proximate to the edge. Accordingly, defects 131, 132, 133 are also discerned by the third transform, but at a lower level of enhancement than defects located on edge 128. Defects 131, 135 (FIG. 2) which is neither on edge 128 nor relatively proximate to the edge, is not discerned by the second transform.

Referring again to FIG. 3, and also to FIGS. 1 and 2, FIG. 3 illustrates that once region of interest 108 of standard 112 has been captured in a data file 232, the data file may be pre-conditioned at step 236 as needed to prepare data file 232 for further processing in accordance with the invention. It is noted that the term "data file" rather than "image file," is used relative to standard 112, since the standard may be contained in a form other than an image, such as a CAD file or other data file. Similar to image file 204, data file 232 may contain only a single region of interest 108 to be processed at this time. Alternatively, data file 232 may be a gross data file containing information regarding entire standard 112 or a portion of the standard smaller than the standard but larger than region of interest 108. In these cases, it may be desirable to extract only information relevant to region of interest 108. Pre-conditioning step 236 may include performing one or more morphological manipulations of data file 232 to account for deformations, if any, introduced into copy 116 by the fabrication process used to make the copy. It is noted that, depending upon the states of data file 232 and copy 116, pre-conditioning step 236 may not need to be performed.

After data file 232 has been preconditioned, if at all, it may be conditioned at steps 240(1), 240(2), . . . 240(n) using the predetermined transforms used to condition image file 204 and create n conditioned image files 216(1), 216(2), . . . 216(n). The result of this conditioning is n conditioned data files 244(1), 244(2), . . . 244(n) that are conditioned for analysis of region of interest 108. For example, in connection with the exemplary standard 112 and copy 116 of FIGS. 1 and 2, respectively, data file 232, or portion thereof such as region of interest 108, may be conditioned by each of the first, second and third transforms discussed above relative to first, second and third conditioned image files 216(1), 216(2), 216 (n)(n=3) so as to create, respectively, conditioned data file 244(1) that serves as a template that enhances the extraction of defects inside defined structure 120, conditioned data file 244(2) that serves as a template that enhances the extraction of defects inside absence 124 of the defined structure and conditioned data file 244(n) (n=3) that provides a template for enhancing the extraction of defects on edge 128 of defined structure 120. It is noted that additional transforms (not shown) may be applied to both data file 232 and image file 204 to further characterize the observed defects.

Figure 4B:
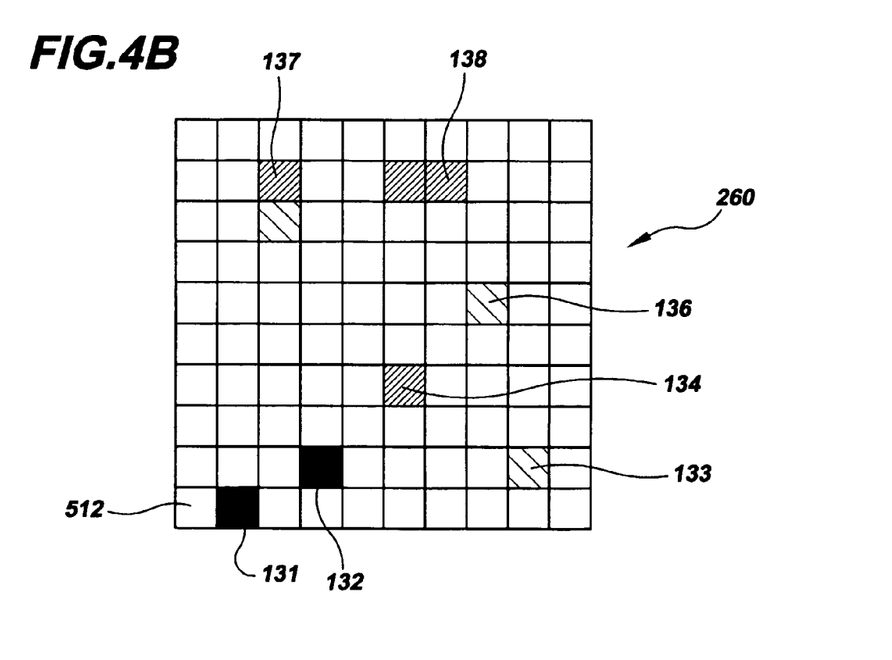
FIG. 4B is a residue image resulting from the extraction of the defects from the conditioned image of FIG. 4A.
Figure 5B:
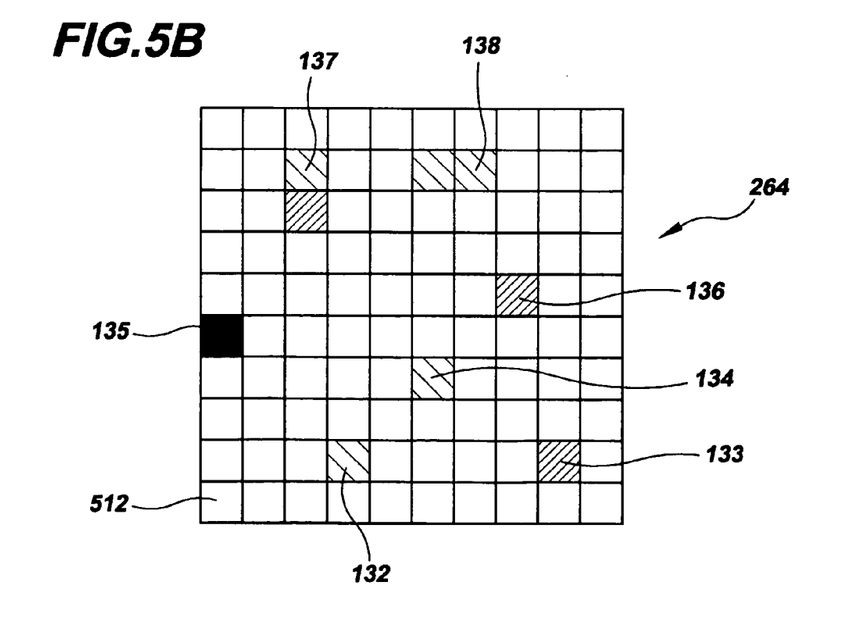
FIG. 5B is a residue image resulting from the extraction of the defects from the conditioned image of FIG. 5A.
Figure 6B:
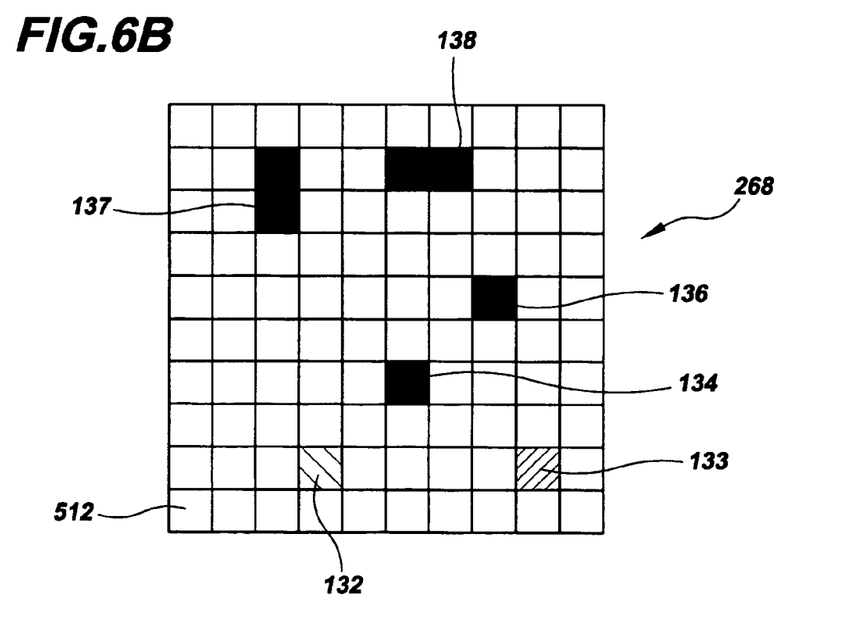
FIG. 6B is a residue image resulting from the extraction of the defects from the conditioned image of FIG. 6A.
Figure 7:
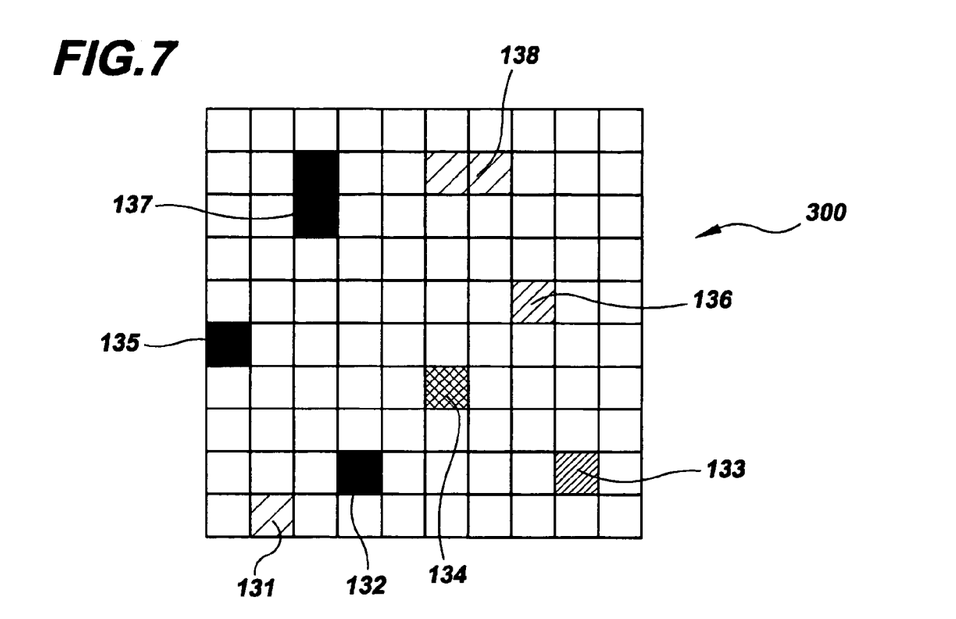
FIG. 7 is a composite image of the residue images of FIGS. 4B, 5B and 6B.

After conditioned image and data files 216(1), 216(2), . . . 216(n), 244(1), 244(2), . . . 244(n) have been created, at step 248 each conditioned image file 216(1), 216(2), . . . 216(n) may be aligned with the corresponding respective conditioned data file 244(1), 244(2), . . . 244(n) so that a corresponding residual defect signal (file) 252(1), 252(2), . . . 252(n) containing defect information may be extracted at step 256, e.g., by subtracting each conditioned image file from the corresponding respective conditioned data file. For example, relative to the exemplary standard 112 and copy 116 of FIGS. 1 and 2, conditioned image file 216(1) may be aligned with and subtracted from conditioned data file 244(1) to create a residual defect signal 252(1) containing a residue image 260 (FIG. 4B) in which defects 131, 132 within defined structure 120 have been enhanced and other defects 133, 134, 136, 137, 138 have been observed. Similarly, conditioned image file 216(2) may be aligned with and subtracted from conditioned data file 244(2) to create a residual defect signal 252(2) containing a residue image 264 (FIG. 5B) in which defect 135 within absence 124 of defined structure 120 have been enhanced and other defects 132, 133, 134, 136, 137, 138 have been observed. Likewise, conditioned image file 216(n) (n=3) may be aligned with and subtracted from conditioned data file 244(n) (n=3) to create a residual defect signal 252(n) (n=3) containing a residue image 268 (FIG. 6B) in which defects 134, 136, 137, 138 on edge 128 of defined structure 120 have been enhanced and other defects 131, 132, 133 have been observed. Residual defect signals 252(1), 252(2), . . . 252(n) may be stored in a common database 272 for further analysis and processing, as discussed below. Database 272 may also contain relevant information concerning the characteristics of each defect, such as, but not limited to, location, size, intensity, shape, major axis, minor axis, cluster and type, e.g., a defect completely within defined structure 120, completely outside the defined structure or on edge 128 of the defined structure, among others. It is noted that in some possible, but unlikely circumstances, it may not be required to create n conditioned data files 244(1), 244(2), . . . 244(n) by applying the transforms used to create n conditioned image files 216 (1), 216(2), . . . 216(n). In such circumstances, each conditioned image file 216(1), 216(2), . . . 216(n) may be extracted directly from data file 232 (or portion thereof), either in a raw or preconditioned form, so as to create residual defect signals 252(1), 252(2), . . . 252(n). FIG. 7 illustrates a composite residue image 300 of residual defect signals 252(1), 252(2), . . . 252(n) (n=3) of FIG. 3 resulting from the extraction of conditioned image files 216(1), 216(2), . . . 216(n) (n=3) from the respective conditioned data files 244(1), 244 (2), . . . 244(n) (n=3) and other processing discussed above.

Figure 8:
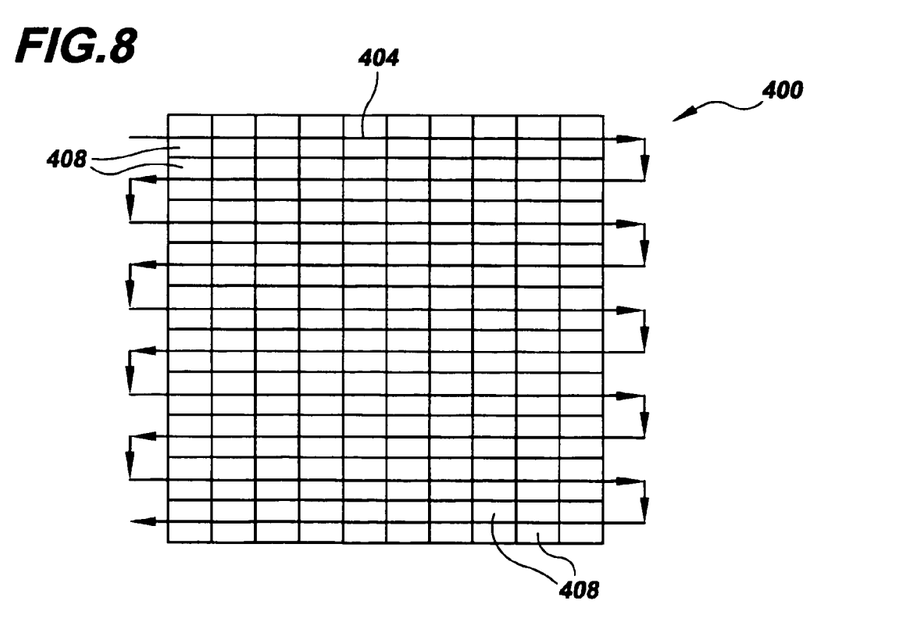
FIG. 8 is a high-level schematic of an overall image of the copy that is composed of a plurality of adjacent regions of interest that may each be subjected to the defect data extraction method of FIG. 3.

Defect extraction method 200 of FIG. 3 discussed above will often be performed on small portions of a gross image of entire copy 216 (FIG. 2) or a portion of the copy larger than region of interest 108 (FIGS. 1 and 2). For example, referring to FIG. 8, defect extraction method 200 has been illustrated with respect to one region of interest 108 that is 10 pixels by 10 pixels in size, whereas the corresponding gross image 400 may be hundreds, thousands or more pixels (or other units) by hundreds, thousands or more pixels (units). If it is desired to analyze one or more larger regions of gross image 400 or the entire gross image, defect extraction method 200 may be performed in an ordered manner, such as in the reciprocating scan-pattern 404 illustrated in FIG. 8 in which individual regions of interest 408 are processed sequentially in the manner discussed above in connection with defect extraction method 200 of FIG. 3. Of course, the plurality of regions of interest 408 may be processed in other orders as desired.

Figure 9:
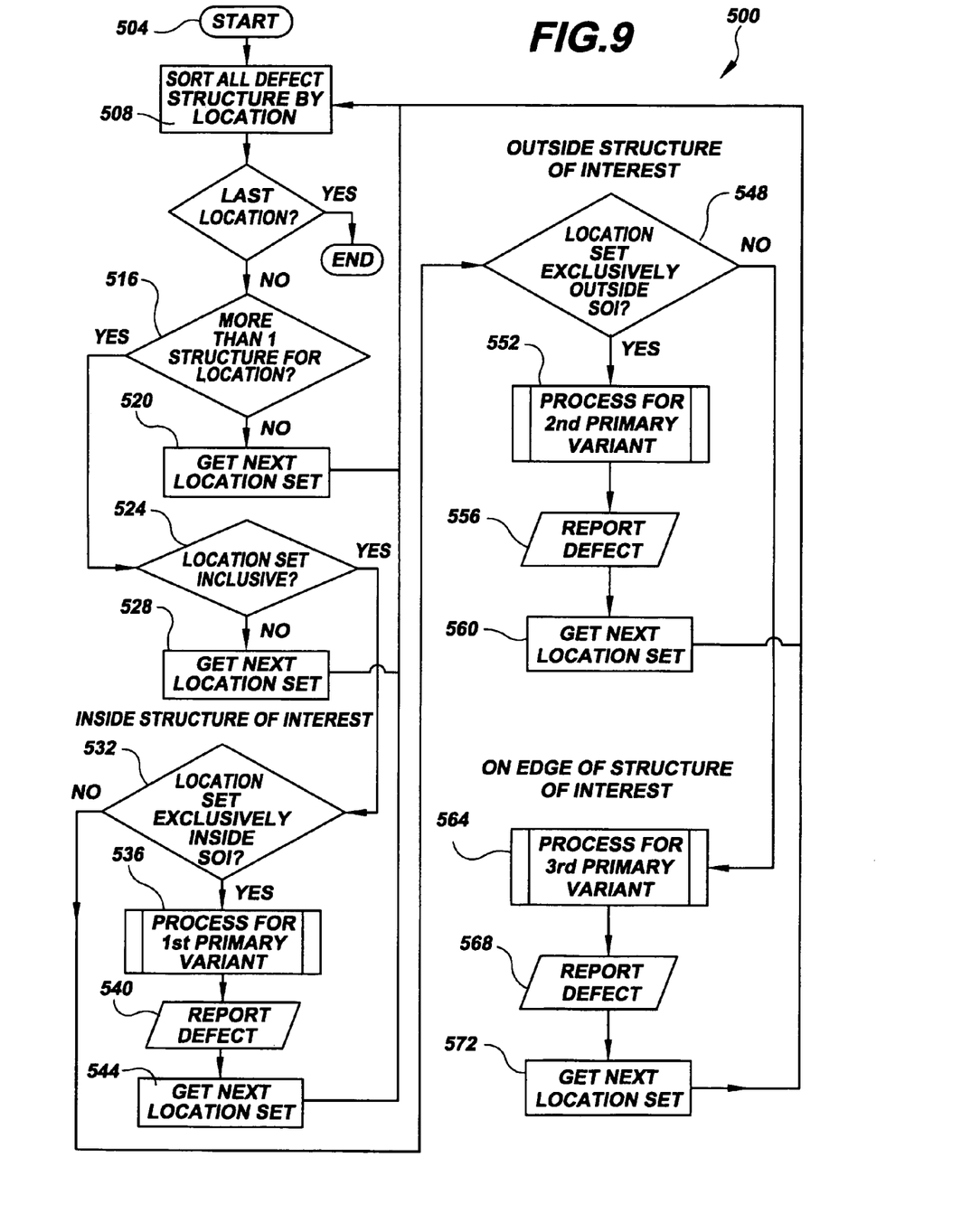
FIG. 9 is a flow chart illustrating a multi-variant image analysis and defect reporting method of the present invention.

Referring to FIG. 9, and also occasionally to FIGS. 1-3 and other figures as noted, FIG. 9 illustrates a rule-based multi-variant data analysis and reporting method 500 of the present invention that may be used to analyze and report defects contained in the number n of residual defect signals 252(1), 252(2), . . . 252(n) generated in defect data extraction method 200 of FIG. 3. As will become apparent, analysis and reporting method 500 is described particularly in connection with the type of defects discussed above in connection with standard 112 and copy 116 of FIGS. 1 and 2, respectively, i.e., defects that are either: 1) contained exclusively within defined structure 120; 2) contained exclusively in absence 124 of the defined structure or 3) on edge 128 of the defined structure. However, those skilled in the art will understand that these types of defects may be replaced and/or supplemented by other types of defects depending upon the type and character of copy 116 and standard 112 under consideration, and will understand the modifications of analysis and reporting method 500 that must be made to accommodate these other types.

As mentioned above relative to defect data extraction method 200, residual defect signals 252(1), 252(2), . . . 252(n) will typically, but not necessarily, be stored in a common database 272. Analysis and reporting method 500 may be started at step 504, e.g., by initiating a program, program module, routine or other program segment or energizing an analysis circuit (not shown) that executes the method. Once this is done, the substantive steps of analysis and reporting method 500 may proceed as follows. At step 508, all residual defect signals 252(1), 252(2), . . . 252(n) extracted by defect data extraction method 200 (FIG. 3) may be processed to sort all defects by their locations. For example, in the context of the pixel-wise representation described above in connection with the application of defect data extraction method 200 (FIG. 3) to standard 112 and copy 116 of FIGS. 1 and 2, the defects may be sorted by location in the 10×10 pixel array, e.g., identifying the lower left hand corner pixel 512 of each residue image 260, 264, 268 (FIGS. 4B, 5B, 6B) as pixel location 1, 1. Thus, e.g., referring to FIG. 7, defect 131 (FIG. 2) may be said to be located at pixel location 1, 5, defect 132 may be said to be located at pixel location 2, 1, and so on.

At step 514, a test is performed to determine whether or not all of the locations, e.g., pixel locations, have been processed in the remaining steps of method 500. If so, method 500 ends at step 515. However, if all of the locations have not been processed, method proceeds to step 516, wherein a test may be performed to determine if each observed defect was reported by only one of the n residual defect signals 252(1), 252(2), . . . 252(n). If only one of residual defect signals 252(1), 252(2), . . . 252(n) reported that defect, then at step 520 the next defect is reviewed. If more than one of defect signals 252(1), 252(2), . . . 252(n) reports a defect, then at step 524 a test may be performed to determine if the set of residual defect signals, i.e. two or more of residual defect signals 252(1), 252(2), . . . 252(n), analyzed thus far is inclusive, i.e., if all n residual defect signals containing that defect have been identified. If the set of residual defect signals is not inclusive, then at step 528 the next available residual defect signal is analyzed to determine if it identifies the defect at issue.

On the other hand, if the set of the defect residual signals that identify the defect at issue is inclusive, then at step 532 a test may be performed to determine whether the location of that defect, as represented in all of the residual defect signals of the set, is exclusively inside a first structure of interest, e.g., defined structure 120 of FIGS. 1 and 2. If the set of residual defect signals is exclusively inside defined structure 120, the signal set may be processed at step 536 for the first primary variant (i.e., the presence of a defect exclusively within the defined structure). The identified defects may then be reported at step 540, and the analysis goes at step 544 to the next residual defect signal, e.g., one of residual defect signals 252(2) . . . 252(n). If the set of residual defect signals is not exclusively inside defined structure 120, then at step 548 a test may be performed to determine whether the set is exclusively outside the defined structure.

If the set of residual defect signals is exclusively outside defined structure 120, the signal set may be processed at step 552 for the second variant (i.e., the presence of a defect exclusively within the defined structure), the defect is reported at step 556 and then the analysis goes to next residual defect signal available at step 560. If, at this point, the set of residual defect signals is not exclusively inside or outside defined structure, then it may be inferred to be on edge 128 of defined structure 120. Accordingly, at step 564 the set of residual defect signals is processed for the third variant (i.e., the presence of a defect on edge 128 of defined structure 120), at step 568 the defect is reported, and at step 572 the analysis advances to the next residual defect signal. The analysis continues through foregoing steps until all residual defect signals in database 272 have been processed. Subsequent analysis and reporting of defects by unique multi-variant characteristics is available to the user. At the completion, i.e., at step 515, of method 500, each variant is contained in its related report (steps 540, 556, and 564). These reports may be further refine to product specific end user classifications, e.g., extra structure or missing structure may be reported based on size criteria, location or some other characteristic that is important to the end user.

FIG. 10 illustrates an exemplary embodiment of an inspection system 600 of the present invention that may be used to capture an image (not shown) of copy 116 (FIG. 2). This captured image may be used as image 104 (FIG. 2) itself or for extracting image 104 for use in defect extraction method 200 of FIG. 3. When data file 232 (FIG. 3) contains a "golden image" of standard 112 (FIG. 1), inspection system 600 may also be used for capturing image 100 of the standard that becomes the golden image, perhaps with the assistance of editing to remove any defects, resulting from the capturing process or otherwise, that would affect an analysis performed in accordance with the present invention.

Inspection system 600 may include a detector 604, such as a CCD camera, among others, and a stage system 608, having, e.g., X and Y stages 612, 616, for supporting and, optionally moving, a subject substrate (not shown) that contains copy 116 (FIG. 2) (or standard 112 (FIG. 1)) during capture of the image. If stage system 608 includes movable stages, such as X and Y stages 612, 616, the stage system may further comprise a position measuring device 620 for determining the position of each of the X and Y stages and motor drives 622 for driving each of the X and Y stages. Inspection system 600 may also include a system controller 624 for controlling the movements of X and Y stages 612, 616 and for controlling the capturing of images using detector 604. In these connections, system controller 624 may comprise a motion controller 628 for controlling the movements of X and Y stages 612, 616 and a frame grabber 632 for capturing images from detector 604.

To conduct an inspection, a subject substrate may be engaged with stage system 608 and irradiated with electromagnetic energy, e.g., white light. Of course, depending upon the characteristics of the subject substrate and/or the characteristics of copy 116 (or standard 112) on the substrate, and, of course, the type of detector 604, the subject substrate may be irradiated with energy other than white light, such as spectrally conditioned light, laser beam, acoustical beam or a charged particle beam, among others. During the inspection, an image signal (file) for use as image file 204 (FIG. 3) or data file 232, or for creating image file 204 or data file 232, may be created using detector 604, stage system 608 and system controller 624 and stored in a suitable storage location (not shown) by frame grabber 632.

Referring to FIGS. 10 and 3, inspection system 600 may further include a processing system 636 for processing image and data files 204, 232 in the manner discussed above in connection with defect extraction method 200 of FIG. 3. Processing system 636 may also digitally store and process, respectively, the (digital) signals (not shown) of conditioned image files 216(1), 216(2), . . . 216(n) and conditioned data files 244(1), 244(2), . . . 244(n). Conditioned data files 244(1), 244(2), . . . 244(n) and their respective conditioned image files 216(1), 216(2), . . . 216(n) may be stored in a suitable storage location (not shown), wherein processing system 636 aligns the corresponding files, extracts residual defect signals 252(1), 252(2), . . . 252(n) and stores them in database 272. Any defect residue present in any one or more of residual defect signals 252(1), 252(2), . . . 252(n) may be considered raw defects. Such defect residue may then be analyzed as described above relative to defect analysis and reporting method 500 of FIG. 9 to extract characteristic data on a per-location, e.g., per-pixel, basis. In one embodiment, processing system 636 may also include a defect data buffer 640 to hold information concerning the defects identified, and a master controller 644 for controlling the entire inspection process from capturing the image(s), performing defect extraction method 200 of FIG. 3 and performing defect analysis and reporting method 500 of FIG. 9.

Skilled artisans will appreciate that the overall process of the present invention described above provides for rapid and accurate inspection of workpieces and devices (i.e., copies) for identification of defects having, e.g., the following characteristics: a) light colored image defects against any background; b) dark colored image defects against any background; and c) edge profile defects against any background. The process of the present invention is non-destructive. Because this process provides the ability to simultaneously or independently optimize the inspection of light colored image defects against any background, dark colored image defects against any background, or edge profile defects against any background, such defects may be detected in parallel. The technique is accordingly well-suited to identifying several different types of defects that are not normally detectable by present inspection methods. Furthermore, the number of inaccurate classification of defects is reduced with the present invention. These and other advantages will become apparent to a skilled artisan after reading this disclosure.

Although the invention has been described and illustrated with respect to an exemplary embodiment thereof, it should be understood by those skilled in the art that the foregoing and various other changes, omissions and additions may be made therein and thereto, without parting from the spirit and scope of the present invention.

What is claimed is:

1. A method of inspecting a copy for defects of interest, comprising the steps of:
   a) providing an image signal containing a region of interest of the copy;
   b) transforming said image signal by a plurality of transform functions so as to obtain a plurality of conditioned image signals;
   c) extracting a plurality of residual defect signals using said plurality of conditioned image signals to determine the presence of defects of interest, wherein each residual defect signal of said plurality of residual defect signals corresponds to a respective one of said plurality of conditioned image signals; and
   d) performing a rule-based analysis on said plurality of residual defect signals;
   wherein:
   step c) includes:
      e) providing a data signal containing said region of interest of a standard; and
      f) extracting each residual defect signal of said plurality of residual defect signals using a corresponding one of said plurality of first conditioned images and said data signal; and
   step f) includes:
      g) transforms said signal by said plurality of transform functions so as to obtain a plurality of conditioned data signal; and h) extracting said residual defect signal of said plurality of detect signals using corresponding respective ones of said plurality of conditioned data signals and said plurality of conditioned image signals.

2. A method according to claim 1, wherein step h) comprises the step of subtracting each one of said plurality of conditioned image signals from a corresponding respective one of said plurality of conditioned data signals so as to obtain corresponding ones of said plurality of residual defect signals.

3. A method according to claim 1, wherein the copy includes at least one defined structure, at least one absence of said at least one defined structure and at least one edge of said at least one defined structure and the defects of interest include defects within said at least one defined structure, defects within said at least one absence and defects on said at least one edge.

4. A method according to claim 3, wherein said plurality of transforms comprises a first transform that enhances the defects of interest within said at least one defined structure, a second transform that enhances the defects of interest within said at least one absence and a third transform that enhances the defects of interest on said at least one edge.

5. A method according to claim 1, further comprising prior to step b) the step of preconditioning said image signal.

6. A method according to claim 5, wherein the step of preconditioning said image signal includes applying geometric corrections to said image signal.

7. A method according to claim 5, wherein the step of preconditioning said image signal includes applying photometric corrections to said image signal.

8. A method according to claim 1, further comprising prior to step g) the step of preconditioning said data signal.

9. A method according to claim 8, wherein the step of preconditioning said image signal includes performing a morphology.

10. A method according to claim 1, wherein said image signal contains at least a portion of a CAD file.

11. A method according to claim 1, wherein said image signal contains at least a portion of a golden image.

12. A method according to claim 1, wherein the copy includes at least one defined structure, at least one absence of said at least one defined structure and at least one edge of said at least one defined structure and the defects of interest include defects within said at least one defined structure, defects within said at least one absence and defects on said at least one edge.

13. A method according to claim 12, wherein said plurality of transforms comprises a first transform that enhances the defects of interest within said at least one defined structure, a second transform that enhances the defects of interest within said at least one absence and a third transform that enhances the defects of interest on said at least one edge.

14. A method according to claim 1, wherein said rule-based analysis includes the steps of determining the location of each one of the defects of interest relative to at least one structure of interest within said region of interest and reporting at least some of the defects of interest based upon their locations.

15. A method according to claim 1, wherein said rule-based analysis includes the step of determining whether each of the defects of interest is present in more than one of said plurality of residual defect signals.

16. A method according to claim 15, wherein said rule-based analysis includes the step of reporting only ones of the defects of interest present in more than one of said plurality of residual defect signals.

17. A method according to claim 1, wherein said rule-based analysis includes the step of determining the location of each of the defects of interest relative to one of a defined structure, an absence of said defined structure and an edge of said defined structure.

18. A method according to claim 17, wherein said rule-based analysis includes the steps of determining whether or not a defect of interest is exclusively within a defined structure, exclusively outside of said defined structure, or on an edge of said defined structure.

19. A method of inspecting a copy for defects of interest, comprising the steps of:
   a) providing an image signal containing a region of interest of the copy;
   b) transforming said image signal by a plurality of transform functions so as to obtain a plurality of conditioned image signals;
   c) extracting a plurality of residual defect signals using said plurality of conditioned image signals to determine the presence of defects of interest, wherein each residual defect signal of said plurality of residual defect signals corresponds to a respective one of said plurality of conditioned image signals; and
   d) performing a rule-based analysis on said plurality of residual defect signals;
   wherein:
   the copy includes at least one defined structure, at least one absence of said at least one defined structure and at least one edge of said at least one defined structure and the defects of interest include defects within said at least one defined structure, defects within aid at least one absence and defects on said at least one edge; and
   said plurality of transforms comprises a first transform that enhances the defects of interest within said at least one defined structure, a second transform that enhances the defects of interest within said at least one absence and a third transform that enhances the defects of interest on said at least one edge.

20. A method according to claim 19, wherein step c) includes;
   e) providing a data signal containing said region of interest of a standard; and
   f) extracting each residual defect signal of said plurality of residual defect signals using a corresponding one of said plurality of first conditioned images and said data signal.

21. A method according to claim 20, wherein step f) includes:
   g) transforming said data signal by said plurality of transform functions so as to obtain a plurality of conditioned data signals; and
   h) extracting each residual defect signal of said plurality of defect signals using corresponding respective ones of said plurality of conditioned data signals and said plurality of conditioned image signals.

22. A method according to claim 21, wherein step h) comprises the step of subtracting each one of said plurality of conditioned image signals from a corresponding respective one of said plurality of conditioned data signals so as to obtain corresponding ones of said plurality of residual defect signals.

23. A method according to claim 21, wherein the copy includes at least one defined structure, at least one absence of said at least one defined structure and at least one edge of said at least one defined structure and the defects of interest include defects within said at least one defined structure, defects within said at least one absence and defects on said at least one edge.

24. A method according to claim 23, wherein said plurality of transforms comprises a first transform that enhances the defects of interest within said at least one defined structure, a second transform that enhances the defects of interest within said at least one absence and a third transform that enhances the defects of interest on said at least one edge.

25. A method according to claim 21, further comprising prior to step g) the step of preconditioning said data signal.

26. A method according to claim 25, wherein the step of preconditioning said image signal includes performing a morphology.

27. A method according to claim 19, further comprising prior to step b) the step of preconditioning said image signal.

28. A method according to claim 27, wherein the step of preconditioning said image signal includes applying geometric corrections to said image signal.

29. A method according to claim 27, wherein the step of preconditioning said image signal includes applying photometric corrections to said image signal.

30. A method according to claim 19, wherein said image signal contains at least a portion of a CAD file.

31. A method according to claim 19, wherein said image signal contains at least a portion of a golden image.

32. A method according to claim 19, wherein said rule-based analysis includes the steps of determining the location of each one of the defects of interest relative to at least one structure of interest within said region of interest and reporting at least some of the defects of interest based upon their locations.

33. A method according to claim 19, wherein said rule-based analysis includes the step of determining whether each of the defects of interest is present in more than one of said plurality of residual defect signals.

34. A method according to claim 33, wherein said rule-based analysis includes the step of reporting only ones of the defects of interest present in more than one of said plurality of residual defect signals.

35. A method according to claim 19, wherein said rule-based analysis includes the step of determining the location of each of the defects of interest relative to one of a defined structure, an absence of said defined structure and an edge of said defined structure.

36. A method according to claim 35, wherein said rule-based analysis includes the steps of determining whether or not a defect of interest is exclusively within a defined structure, exclusively outside of said defined structure, or on an edge of said defined structure.

* * * * *